Aug. 30, 1932. W. SIM Plant Pat. 24
VARIETY OF PLANT
Filed Jan. 28, 1931
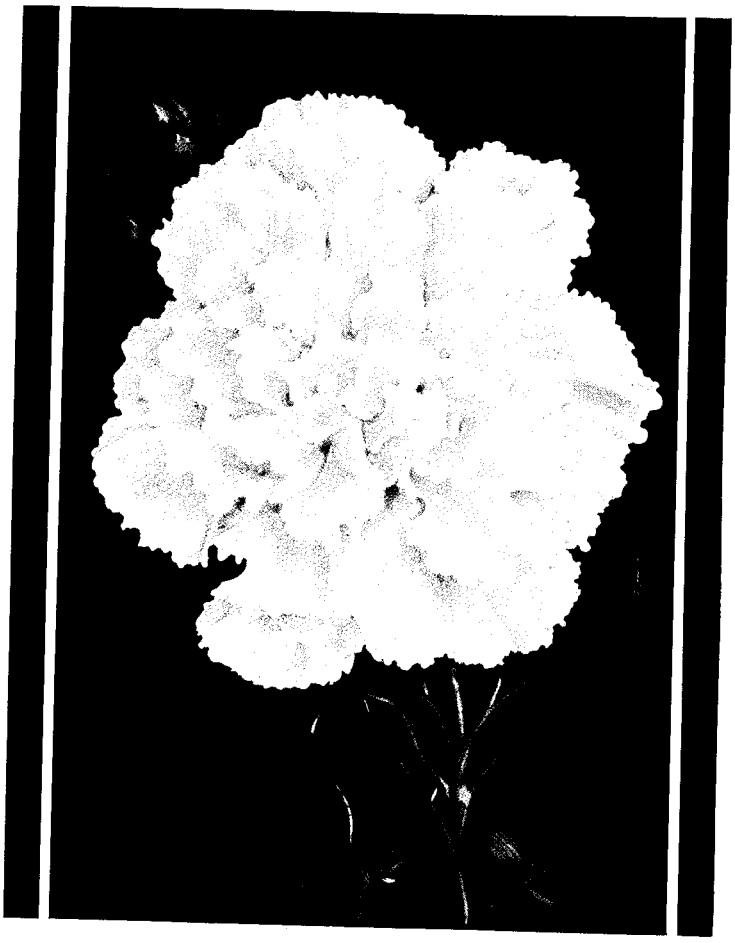
William Sim
by Charles W. Dowell
ATTORNEY Patented Aug. 30, 1932

Plant Pat. 24

UNITED STATES PATENT OFFICE

WILLIAM SIM, OF SAUGUS, MASSACHUSETTS

VARIETY OF PLANT

Application filed January 28, 1931. Serial No. 511,885.

This invention relates to flowering plants, more particularly known as carnations. It has for its objects to create a new and improved variety of carnation; to provide a carnation of novel coloring and vigor; to insure a carnation of increased strength and stronger constitution than has heretofore been known; to provide in carnations a greater endurance and prolonged useful existence after cutting; to insure a continuing stage of beauty and perfection over a greater period of time than has been heretofore known; to increase the useable life of carnations after cutting; to provide a healthy free flowering, upright growing plant producing carnations of a bronzy yellow suffused with pink and having a white edge, and to provide the various other advantages and results made evident from the following specification.

I have accomplished the objects of my invention in this specific instance by crossing so called two unnamed seedlings. That is to say, two distinct unnamed seeds were first planted and allowed to mature in plant form to the flowering stage at which point they represented two distinct varieties of carnations, one only of which was pollen bearing. In event both of the varieties should develop as pollen bearing, the pollen on one must be carefully removed before self fertilization results. At the full bloom stage, the pollen from the pollen bearing variety was transferred by tweezers or other suitable method to the variety without pollen. The resulting seed pod on the variety to which the pollen was transferred was then allowed to mature, and when ripe was sowed or planted. These seed in turn grew and developed into the new variety of carnation herein described.

The drawings represent a characterization of the new variety of carnation herein set forth and described.

The commercial production of my new and improved variety requires a period of five years for observation and development of quantity cuttings.

Having thus described my invention, I claim as new and desire to secure by Letters Patent of the United States of America:—

A carnation as shown and described, characterized by a bronzy yellow color suffused with pink and with a white edge.

In testimony whereof I affix my signature.

WILLIAM SIM.